(12) United States Patent
Buerger et al.

(10) Patent No.: US 10,993,700 B2
(45) Date of Patent: May 4, 2021

(54) MEDICAL IMAGE PROCESSING DEVICE AND METHOD

(71) Applicant: KONINKLIJKE PHILIPS N.V., Eindhoven (NL)

(72) Inventors: Christian Buerger, Hamburg (DE); Irina Waechter-Stehle, Hamburg (DE); Frank Michael Weber, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 578 days.

(21) Appl. No.: 15/314,327

(22) PCT Filed: Jun. 9, 2015

(86) PCT No.: PCT/EP2015/062752
§ 371 (c)(1),
(2) Date: Nov. 28, 2016

(87) PCT Pub. No.: WO2015/189160
PCT Pub. Date: Dec. 17, 2015

(65) Prior Publication Data
US 2018/0235577 A1    Aug. 23, 2018

(30) Foreign Application Priority Data

Jun. 12, 2014  (EP) ..................... 14172051

(51) Int. Cl.
*A61B 8/08*    (2006.01)
*G06T 7/174*    (2017.01)
(Continued)

(52) U.S. Cl.
CPC .......... *A61B 8/5246* (2013.01); *A61B 8/0883* (2013.01); *G06T 7/12* (2017.01);
(Continued)

(58) Field of Classification Search
CPC ....... A61B 8/5246; A61B 8/0883; G06T 7/12; G06T 7/174; G06T 7/149; G06T 7/0012;
(Continued)

(56) References Cited

U.S. PATENT DOCUMENTS 7,031,504 B1  4/2006 Argiro et al.
8,265,363 B2  9/2012 Orderud et al.
(Continued)

OTHER PUBLICATIONS

Introduction to Polygon Meshes. (Apr. 2, 2015). Retrieved Dec. 25, 2015, from https://www.scratchapixel.com/lessons/3d-basic-rendering/introduction-polygon-mesh (Year: 2015).*
(Continued)

*Primary Examiner* — Michael J Tsai
*Assistant Examiner* — Johnathan Maynard (57) ABSTRACT

The present invention relates to a medical image processing device (10), comprising: —a receiving unit (60) for receiving a first and a second medical image (72, 74) of an anatomical object of interest (84), wherein each of the first and the second medical images (72, 74) comprises a different field of view of the anatomical object of interest (84), and wherein the first medical image and the second medical image (72, 74) show a same or similar anatomical state of the anatomical object of interest (84); —a registration unit (64) that is configured to determine a transformation from an image space of the second medical image (74) to an image space of the first medical image (72); —a transformation unit (66) that is configured to transform the second medical image (74) into the image space of the first medical image (72) based on said transformation in order to receive a transformed second medical image (74'); and —a segmentation unit (68) that is configured to perform an overall segmentation that makes use of both the first medical image (72) and the transformed second medical image (74') without fusing the first medical image (72) and the transformed
(Continued)

second medical image (74'), wherein one and the same segmentation model (92) is simultaneously adapted to both the first medical image (72) and the transformed second medical image (74') by identifying a first set of feature points (80) of the anatomical object of interest (84) within the first medical image (72), by identifying a second set of feature points (82) of the anatomical object of interest (84) within the transformed second medical image (74'), and by adapting the segmentation model (92) to both the first and the second set of feature points (80, 82).

15 Claims, 7 Drawing Sheets (51) Int. Cl.
G06T 7/149 (2017.01)
G06T 7/12 (2017.01)
G06T 7/00 (2017.01)
(52) U.S. Cl.
CPC .............. *G06T 7/149* (2017.01); *G06T 7/174* (2017.01); *G06T 7/0012* (2013.01); *G06T 2207/10136* (2013.01); *G06T 2207/20061* (2013.01); *G06T 2207/20112* (2013.01); *G06T 2207/20124* (2013.01); *G06T 2207/30048* (2013.01)
(58) Field of Classification Search
CPC . G06T 2207/20112; G06T 2207/30048; G06T 2207/20124; G06T 2207/10136; G06T 2207/20061
See application file for complete search history.

(56) References Cited

U.S. PATENT DOCUMENTS

| 9,934,579 | B2 | 4/2018 | Prevost et al. | |
|---|---|---|---|---|
| 2008/0249414 | A1* | 10/2008 | Yang | A61B 8/483 600/445 |
| 2009/0156933 | A1* | 6/2009 | Gerard | G06T 7/38 600/443 |
| 2010/0067768 | A1* | 3/2010 | Ionasec | G06T 7/35 382/131 |
| 2010/0195881 | A1* | 8/2010 | Orderud | G06T 7/251 382/131 |
| 2010/0295848 | A1 | 11/2010 | Grewer et al. | |
| 2011/0299750 | A1* | 12/2011 | Cool | G06T 17/10 382/131 |
| 2012/0027277 | A1 | 2/2012 | Vik et al. | |
| 2013/0035596 | A1* | 2/2013 | Ionasec | A61B 8/0883 600/450 |
| 2016/0007970 | A1* | 1/2016 | Dufour | A61B 8/58 600/437 |

OTHER PUBLICATIONS

Ecabert, et al., "Automatic Model-Based Segmentation of the Heart in CT Images", IEEE Transactions on Medical Imaging, vol. 27, No. 9, Sep. 2008, pp. 1189-1201.

Ecabert, et al., Segmentation of the heart and great vessels in CT images using a model-based adaptation framework, Medical Image Analysis, vol. 15, Issue 6, Dec. 2011, pp. 863-876 (Abstract).

Rajpoot, et al., "The evaluation of single-view and multi-view fusion 3D echocardiography using image-driven segmentation and tracking", Medical Image Analysis 15, 2011, pp. 514-528.

Zheng, et al., "Four-Chamber Heart Modeling and Automatic Segmentation for 3D Cardiac CT Volumes Using Marginal Space Learning and Steerable Features", IEEE Transactions on Medical Imaging, pp. 1-14.

Lotjonen, et al., "Statistical shape model of atria, ventricles and epicardium from short-and long-axis MR images", Medical Image Analysis 8, 2004, pp. 371-386.

Hansegard, et al., "Detection of the myocardial boundary in the left ventricle from simultaneously acquired triplane ultrasound images using multi view active appearance motion models", 2005 IEEE Ultrasonic Symposium, pp. 2267-2270.

Lelieveldt, et al., "Multi-view active appearance models for consistent segmentation of multiple standard views: application to long- and short-axis cardiac MR images", International Congress Series 1256 (2003), pp. 1141-1146.

Oost, et al., "Automated Segmentation of X-ray Left Ventricular Angiograms Using Multi-View Active Appearance Models and Dynamic Programming", FIMH 2005, LNCS 3504, 2005, pp. 23-32.

* cited by examiner

MEDICAL IMAGE PROCESSING DEVICE AND METHOD

This application is the U.S. National Phase application under 35 U.S.C. § 371 of International Application No. PCT/EP2015/062752, filed on Jun. 9, 2015, which claims the benefit of European Application Serial No. 14172051.6, filed Jun. 12, 2014. These applications are hereby incorporated by reference herein.

FIELD OF THE INVENTION

The present invention generally relates to the field of medical imaging. In particular, the present invention relates to a medical image processing device for processing two- and/or three-dimensional medical images. The present invention further relates to a corresponding medical image processing method. Still further, the present invention relates to a computer program comprising program code means for causing a computer to carry out the steps of said method. An exemplary technical application of the present invention is the field of 3D ultrasound imaging. However, it shall be noted that the present invention may also be used in medical imaging modalities other than ultrasound imaging, such as, for example, CT, MR or MRI.

BACKGROUND OF THE INVENTION

Medical imaging systems, such as e.g. 2D and 3D ultrasound imaging systems, are well-known. Especially 3D medical imaging has become essential to medical diagnosis practice. By providing concise and relevant information to radiologists and physicians, 3D medical imaging increases clinical productivity. While ultrasound imaging provides a plurality of advantages for the radiologists and physicians, a common problem in the field of ultrasound imaging is the limited field of view of the ultrasound imaging devices.

The limited field of view in ultrasound often does not allow the sonographer to image the complete anatomical object of interest. For example, in transthoracic echocardiography (TTE) imaging applications and in transesophageal echocardiography (TEE) imaging, in which the beating heart is imaged either in two- or three-dimensional form, the limited field of view of the ultrasound devices may be disadvantageous. In this case only a sub-structure of the heart can be imaged in one image frame with good image quality while other structures of the heart cannot be imaged adequately. Ultrasound images of the left side of the heart normally do not show the complete right side of the heart, and vice versa.

In order to quantify the complete heart, multiple acquisitions are thus required, each imaging and quantifying another specific sub-structure of the heart. Image segmentation can only cover these sub-structures, while the missing structures have to be at least partially extrapolated. For instance, in left ventricular centric images the left ventricular volume can be computed while the right ventricle is partially outside the field of view. In contrast thereto, in right ventricular centric images the right ventricular volume can be computed while the left ventricle is partially outside the field of view. Consequently, a quantification of the whole heart is prone to errors.

A similar problem arises in 3D fetal ultrasound applications when the fetus becomes too large to fit in one field of view.

Hence, a single segmentation of the complete anatomical object of interest would be desirable to provide more robust and consistent segmentation results.

Rajpoot, K. et al. present a method for fusing multiple 3D echocardiographic images in order to receive a fused image that contains the whole heart (Rajpoot, K. et al.: "The evaluation of single-view and multi-view fusion 3D echocardiography using image-driven segmentation and tracking", in Medical Image Analysis 15 (2011), pages 514-528). The technique proposes acquiring multiple single-view images and afterwards aligning these images using a standard multi-resolution rigid registration algorithm with normalized cross-correlation as the similarity measure. The first full volume acquired near the application position is used as the reference volume for the registration. Once the image correspondence has been established, the aligned images are combined together. Wavelet analysis technique is used to decompose each single-view image into its low- and high-frequency components. The fusion is then performed in the wavelet domain, treating the low- and high-frequency wavelet coefficients differently. The fused image may then be used for an overall segmentation of the heart.

While the above-mentioned technique provides the possibility to perform a single segmentation of an anatomical object of interest, such as the heart, that does not completely fit into a single field of view of an ultrasound cone beam, this technique still involves several drawbacks. One reason that leads to these drawbacks is that the segmentation is done on the fused image. When combining the images in a common coordinate system as presented by Rajpoot, K. et al., valuable information might get lost because of the introduction of smoothing artefacts and artificial edges at the stitching borders. Although these artefacts may help to increase the signal to noise ratio of the images, they also lead to problems, because tissue transitions from e.g. the blood pool to myocardium is smoothed out as well due to imperfections in the registration-based image alignments. The fusion of the images furthermore causes intensity discrepancies and may lead to artificial walls/edges that may distort the segmentation. The image fusion furthermore leads to unwanted smoothing effects.

Thus, there is still room for improvement.

SUMMARY OF THE INVENTION

It is an object of the present invention to provide an improved medical image processing device and corresponding method which substantially alleviate or overcome the above-mentioned deficiencies. It is particularly an object of the present invention to provide a medical image processing device and corresponding method that enable segmenting a whole anatomical object of interest, such as heart or a fetus, in a single segmentation, even if each of a set of acquired images only shows a part or sub-structure of the anatomical object of interest due to a limited field of view.

According to a first aspect of the present invention, a medical image processing device is presented that comprises:

a receiving unit for receiving a first and a second medical image of an anatomical object of interest, wherein each of the first and the second medical images comprises a different field of view of the anatomical object of interest, and wherein the first medical image and the second medical image show a same or similar anatomical state of the anatomical object of interest;

a registration unit that is configured to determine a transformation from an image space of the second medical image to an image space of the first medical image;

a transformation unit that is configured to transform the second medical image into the image space of the first medical image based on said transformation in order to receive a transformed second medical image; and a segmentation unit that is configured to perform an overall segmentation that makes a separate use of both the first medical image and the transformed second medical image (without fusing the first medical image and the transformed second medical image), wherein one and the same segmentation model is simultaneously adapted to both the first medical image and the transformed second medical image by identifying a first set of feature points of the anatomical object of interest within the first medical image, by identifying a second set of feature points of the anatomical object of interest within the transformed second medical image, and by adapting the segmentation model to both the first and the second set of feature points.

According to a second aspect of the present invention, a medical image processing method is presented, wherein in the method comprises the steps of:

receiving a first medical image and a second medical image of an anatomical object of interest, wherein each of the first and the second medical images comprises a different field of view of the anatomical object of interest, and wherein the first medical image and the second medical image show a same or similar anatomical state of the anatomical object of interest;

determining a transformation from an image space of the second medical image to an image space of the first medical image;

transforming the second medical image into the image space of the first medical image based on said transformation in order to receive a transformed second medical image; and performing an overall segmentation that makes a separate use of both the first medical image and the transformed second medical image (without fusing the first medical image and the transformed second medical image), wherein one and the same segmentation model is simultaneously adapted to both the first medical image and the transformed second medical image by identifying a first set of feature points of the anatomical object of interest within the first medical image, by identifying a second set of feature points of the anatomical object of interest within the transformed second medical image, and by adapting the segmentation model to both the first and the second set of feature points.

According to a still further aspect of the present invention, a computer program is presented comprising program code means for causing a computer to carry out the steps of the above-mentioned method when said computer program is carried out on the computer.

Preferred embodiments of the invention are defined in the dependent claims. It shall be understood that the claimed method and the claimed computer program have similar and/or identical preferred embodiments as the claimed medical image processing device and as defined in the dependent claims.

It is to be noted that the present invention applies to both off-line and live image processing. The receiving unit may thus receive the medical images either from any type of internal or external storage unit in an off-line mode, or it may receive the medical images directly from an image acquisition unit, e.g. from an ultrasound imaging apparatus, in a live image processing mode.

The term "medical image" shall refer to an image (frame of an image sequence) of a body part of a patient that is produced by a medical imaging apparatus of any modality, such as ultrasound imaging, CT imaging, MR imaging or MRI imaging.

The term "anatomical object of interest" shall refer to any anatomical object of a patient, such as the heart, any other organ or to a fetus.

The medical images processed by the medical image processing device may either be 2D or 3D images. According to a preferred embodiment, the medical images include 3D TTE images, 3D TEE images, or 3D fetal ultrasound images.

It shall be furthermore noted that the present invention is described by processing a first and a second medical image. The terms "first" and "second" shall not imply a time-based or type-based delimitation, but are rather used herein to differentiate between two exemplary medical images. It is clear that in practice several medical images may be processed by means of the presented device, and not only a first and a second medical image (even though this is possible as well).

The definition that the first medical image and the second medical image show a "same or similar anatomical state" of the anatomical object of interest shall mean that both images show the anatomical object of interest in the same or similar temporal, anatomical or motional state. In case the anatomical object of interest is the heart, both images shall show the heart, e.g. different sub-structures of the heart, in a common cardiac phase or common motion state, e.g. in the end-diastolic or end-systolic phase. However, it shall be noted that the first and second image do not have to belong to the same cardiac cycle, but may also be derived from different cardiac cycles as long as they show the heart in the same cardiac phase or motion state.

The present invention is based on the idea to generate a single segmentation of the whole anatomical object of interest from at least two complementary images, preferably from multiple complementary images which comprise different field of views of the anatomical object of interest. The presented device and method so to say generate a single segmentation of the whole anatomical object of interest as a combination of at least two, preferably multiple sub-segmentations.

In case of two medical images (a first and a second medical image), the registration unit thereto determines in a first step a transformation from the image space of the second medical image to the image space of the first medical image. The image space of the first medical image may so to say be regarded as the reference image space. This transformation is preferably realized as a rigid transformation which translates and/or rotates the second medical image into the image space of the first medical image.

The transformation is preferably determined by means of a point-to-point and/or mesh-to-mesh registration, as this will be elucidated further below in detail. However, the transformation could generally also be determined by applying an image-based registration, even though this is not preferred in the present case. The result of the registration will be a transformation matrix that parametrically describes how the image space of the second medical image may be transformed into the image space of the first medical image.

This transformation is used within the transformation unit to transform the second medical image into the image space of the first medical image. The transformation unit in other words translates and/or rotates the second medical image into the image space of the first medical image in order to receive two aligned images in the same reference image space. The result of the transformation of the second medical image is herein denoted as transformed second medical image.

In the last step, the segmentation unit uses both the first medical image as well as the transformed second medical image for an overall segmentation of the complete anatomical object of interest. The segmentation unit thereto applies a model-based segmentation.

One of the central ideas of the present invention is that for this overall segmentation one and the same segmentation model is simultaneously adapted to both the first medical image as well as to the transformed second medical image. It is important to note that the first medical image and the transformed second medical image are not fused together (they are being processed independently). The first and the transformed second medical image are still separated within the memory of the medical image processing device. The first and the transformed second medical image are so to say still separately stored in two different layers. However, the segmentation unit uses a single segmentation model that is simultaneously adapted to both the first medical image and the transformed second medical image. This is one of the major differences to the approach proposed by Rajpoot, K. et al. that has been presented in the introductory portion of the description. Rajpoot, K. et al. proposes to fuse the images in order to generate a fused image, wherein the fused image is afterwards segmented.

Since the presented device does not fuse both images, but nevertheless bases the segmentation on both images using one and the same segmentation model, the disadvantages of an image fusion (e.g. the inclusion of artefacts and artificial walls, intensity discrepancies and image smoothing) may be prevented, while it is still possible to generate a single segmentation of the whole anatomical object of interest. The presented device and method therefore lead to more robust and more consistent segmentation results which may be used for the quantification of the anatomical object of interest.

The presented device and method so to say use the best of each medical image without fusing them. The single segmentation of the whole anatomical object of interest is computed from different images showing different field of views, such that each sub-structure is segmented from those images where it is visible in.

The segmentation unit preferably performs the overall segmentation by:
  identifying a first set of feature points of the anatomical object of interest within the first medical image,
  identifying a second set of feature points of the anatomical object of interest within the transformed second medical image, and
  adapting the segmentation model simultaneously to both the first and the second set of feature points.

The segmentation mesh-model is thus deformed to match the feature points identified in both images. In case of segmenting a fused image as proposed by Rajpoot, K. et al., the segmentation mesh-model would only be deformed to match one set of feature points identified in the single fused image, whereas according to the present invention the segmentation mesh-model is deformed to match at least two sets of feature points (in case of two images). It should be evident that this leads to more robust and more consistent segmentation results.

The first and the second set of feature points of the anatomical object of interest are preferably identified by identifying within each of the first medical image and the transformed second medical image, the image points having the highest brightness gradients within each of the first medical image and the transformed second medical image, respectively. However, it shall be noted that the brightness gradient is or does not have to be the only indicator for the identification of the feature points. The identification may be also based on other criteria, such as the absolute values of the pixel brightness, or on an algorithm that compares the brightness of the pixels within the segmentation mesh to the brightness of the pixels outside of the segmentation mesh. However, using the image brightness gradient for the segmentation may be realized in a fairly easy manner. The segmentation may thus look in the images for bright-to-dark edges (or dark-to-bright edges), which usually represent the direction of tissue borders in the images, i.e. the boundaries of the anatomical features of the anatomical object of interest.

As it has been already mentioned above, the present invention is of course not limited to process only two medical images in the above-mentioned way. Preferably, multiple medical images are used for the above-mentioned overall segmentation. The principle, however, stays the same. The plurality of images are first registered into a reference space, e.g. in the image space of one of the images. Inter-field-of-view transformations are thus computed for all images in order to describe the geometric transformation of all field of views to the common reference space. All images will then be transformed by means of their respective inter-field-of-view transformation, such that all images are aligned with each other. The segmentation unit will then perform an overall segmentation, as explained before, by making use of all images transformed into the reference space and applying only one segmentation model that is simultaneously adapted to all images in the reference space.

According to a further embodiment, the segmentation unit is configured to perform, prior to the overall segmentation, an individual segmentation of the first medical image in order to receive a first segmentation mesh, as well as to perform an individual segmentation of the second medical image in order to receive a second segmentation mesh. The registration unit is in this case configured to determine the transformation from the image space of the second image to the image space of the first image by applying a point-based registration of the second segmentation mesh onto the first segmentation mesh.

It is important to note that the above-mentioned individual segmentations of the first and the second medical image are not connected to the overall segmentation that is simultaneously adapted to both the first medical image and the transformed second medical image. The individual segmentations of the first and the second medical image are done for a different technical purpose than the overall segmentation. The individual segmentations of all medical images are applied before each image is registered to the reference space. These segmentations shall facilitate the determination of the inter-field-of-view transformations, e.g. the transformation from the image space of the second medical image to the image space of the first medical image. In other words, the individual segmentation of each image enables determining the transformation of each image by using a rigid point-based mesh-to-mesh registration. Such a mesh-tomesh registration is faster and more accurate than an image-based registration that would have to be performed without the individual segmentations of each image.

The segmentation unit is preferably configured to apply the same segmentation model for the individual segmentation of the first medical image and the second medical image. The overall segmentation makes use of a slightly different segmentation model which uses two sets (rather than one) of trained image features, one set for each image to segment. Note that in this application where only the field of view is changing, the two sets are the same and equal to the one of the single image segmentation models.

According to a further embodiment, the receiving unit is configured to receive a first medical image sequence including the first medical image and a second medical image sequence including the second medical image, wherein the medical image processing device further comprises a selection unit for selecting the first and the second medical image in order to identify corresponding images of the same or similar anatomical state of the anatomical object of interest.

As already explained above, the medical image processing device is in practice often directly connected to a medical imaging apparatus, such as an ultrasound device. In this case, the receiving unit does not directly receive the first and the corresponding second medical image, which show the same or similar anatomical state of the anatomical object of interest, but rather receives several image sequences. For example, a sonographer starts acquiring the first medical image sequence with a first field of view of a sub-structure of the beating heart, such as the beating of the left ventricle. Next, the sonographer acquires the second medical image sequence with a second field of view that shows another sub-structure of the beating heart, such as the beating of the right ventricle. This procedure is repeated until all structures of interest have been imaged. It is then important to identify corresponding images of the same cardiac phase, e.g. the end-diastolic or the end-systolic phase. This may be done by means of the above-mentioned selection unit. The selection unit may allow selecting the corresponding images (i.e. the first and the second medical image) either in a manual way or by means of an automatic approach.

The automatic approach may be implemented as follows: The segmentation unit may be configured to individually segment all images of the first and the second medical image sequence, wherein the selection unit is configured to automatically select the first and the second medical image based on a segmentation of all images of the first and the second medical image sequence. The selection unit may, for example, be configured to derive a volume curve for each image sequence from the segmentation of all images within the corresponding image sequence. The comparison of these volume curves then enables to automatically pick out an image of each image sequence showing the heart in a certain cardiac phase.

According to a further embodiment, the medical image processing device may further comprise an image construction unit that is configured to reconstruct a fused image by fusing the first medical image and the transformed second medical image. This may allow to visualizing an image of the whole anatomical object of interest, similar as proposed by Rajpoot, K. et al. The fused image may be provided by the presented medical image processing device as an add-on only. It has to be noted that the overall segmentation that may be used for the quantification of the anatomical object of interest is in this case still not based on the fused image, but generated according to the approach explained above.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Before referring to the medical image processing device 10 according to the present invention, the basic principles of an ultrasound system 100 shall be explained with reference to FIGS. 1 and 2. Even though the field of ultrasound imaging is a preferred application of the herein presented medical image processing device 10, the presented medical image processing device 10 is not limited to the field of ultrasound imaging. The herein presented device 10 may also be used in other medical imaging modalities, such as, for example, CT, MR, MRI, etc.

Figure 1:
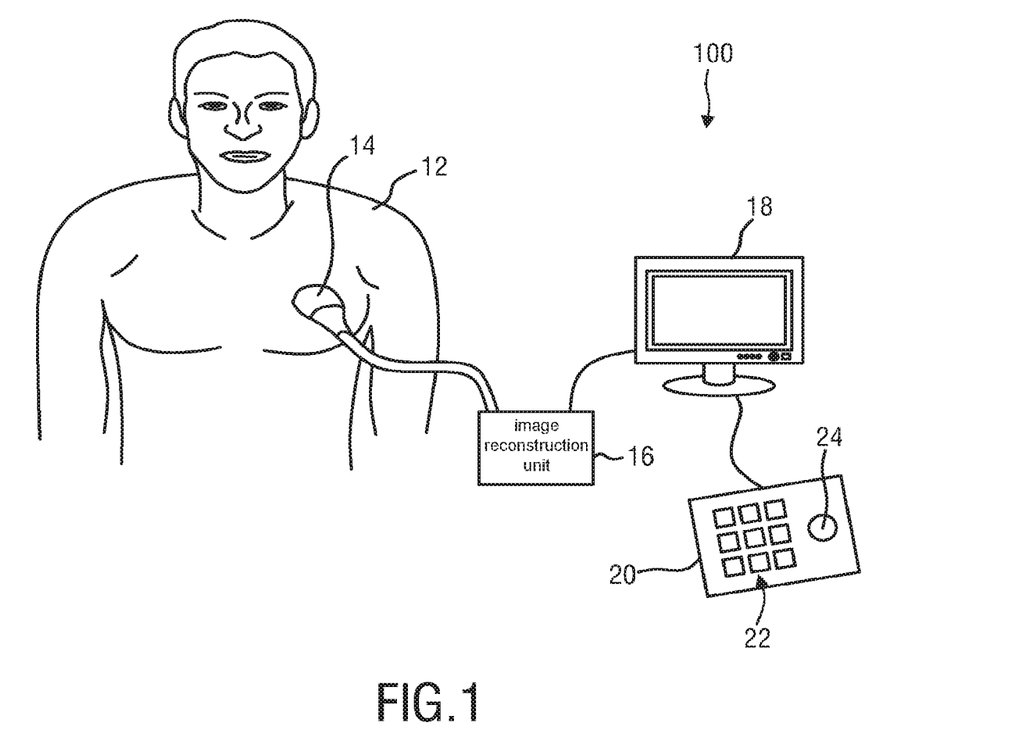
FIG. 1 shows a schematic representation of an ultrasound imaging system in use to scan a part of a patient's body.

FIG. 1 shows a schematic illustration of an ultrasound system 100, in particular a medical three-dimensional (3D) ultrasound imaging system. The ultrasound imaging system 100 is applied to inspect a volume of an anatomical site, e.g. a heart of a patient 12. The ultrasound system 100 comprises an ultrasound probe 14 having at least one transducer array having a multitude of transducer elements for transmitting and/or receiving ultrasound waves. In one example, each of the transducer elements can transmit ultrasound waves in form of at least one transmit impulse of a specific pulse duration, in particular a plurality of subsequent transmit pulses. The transducer elements are preferably arranged in a two-dimensional array, in particular for providing a multi-planar or three-dimensional image.

A particular example for a three-dimensional ultrasound system which may be applied for the current invention is the CX40 Compact Xtreme ultrasound system sold by the applicant, in particular together with a X6-1 or X7-2t TTE transducer of the applicant or another transducer using the xMatrix technology of the applicant. In general, matrix transducer systems as found on Philips iE33 systems or mechanical 3D/4D transducer technology as found, for example, on the Philips iU22 and HD15 systems may be applied for the current invention.

A 3D ultrasound scan typically involves emitting ultrasound waves that illuminate a particular volume within a body, which may be designated as target volume. This can be achieved by emitting ultrasound waves at multiple different angles. A set of volume data is then obtained by receiving and processing reflected waves. The set of volume data is a representation of the target volume within the body over time. Since time is usually denoted as fourth dimension, such ultrasound system 100 delivering a 3D image sequence over time, is sometimes also referred to a 4D ultrasound imaging system.

It shall be understood that the ultrasound probe 14 may either be used in a non-invasive manner (as shown in FIG. 1) or in an invasive manner as this is usually done in TTE (not explicitly shown). The ultrasound probe 14 may be hand-held by the user of the system. The ultrasound probe 14 is applied to the body of the patient 12 so that an image of an anatomical object of interest is provided.

Further, the ultrasound system 100 may comprise an image reconstruction unit 16 that controls the provision of a 3D image sequence via the ultrasound system 100. As will be explained in further detail below, the image reconstruction unit 16 controls not only the acquisition of data via the transducer array of the ultrasound probe 14, but also signal and image processing that form the 3D image sequence out of the echoes of the ultrasound beams received by the transducer array of the ultrasound probe 14.

The ultrasound system 100 may further comprise a display 18 for displaying the 3D image sequence to the user. Still further, an input device 20 may be provided that may comprise keys or a keyboard 22 and further input devices, for example a trackball 24. The input device 20 may be connected to the display 18 or directly to the image reconstruction unit 16.

Figure 2:
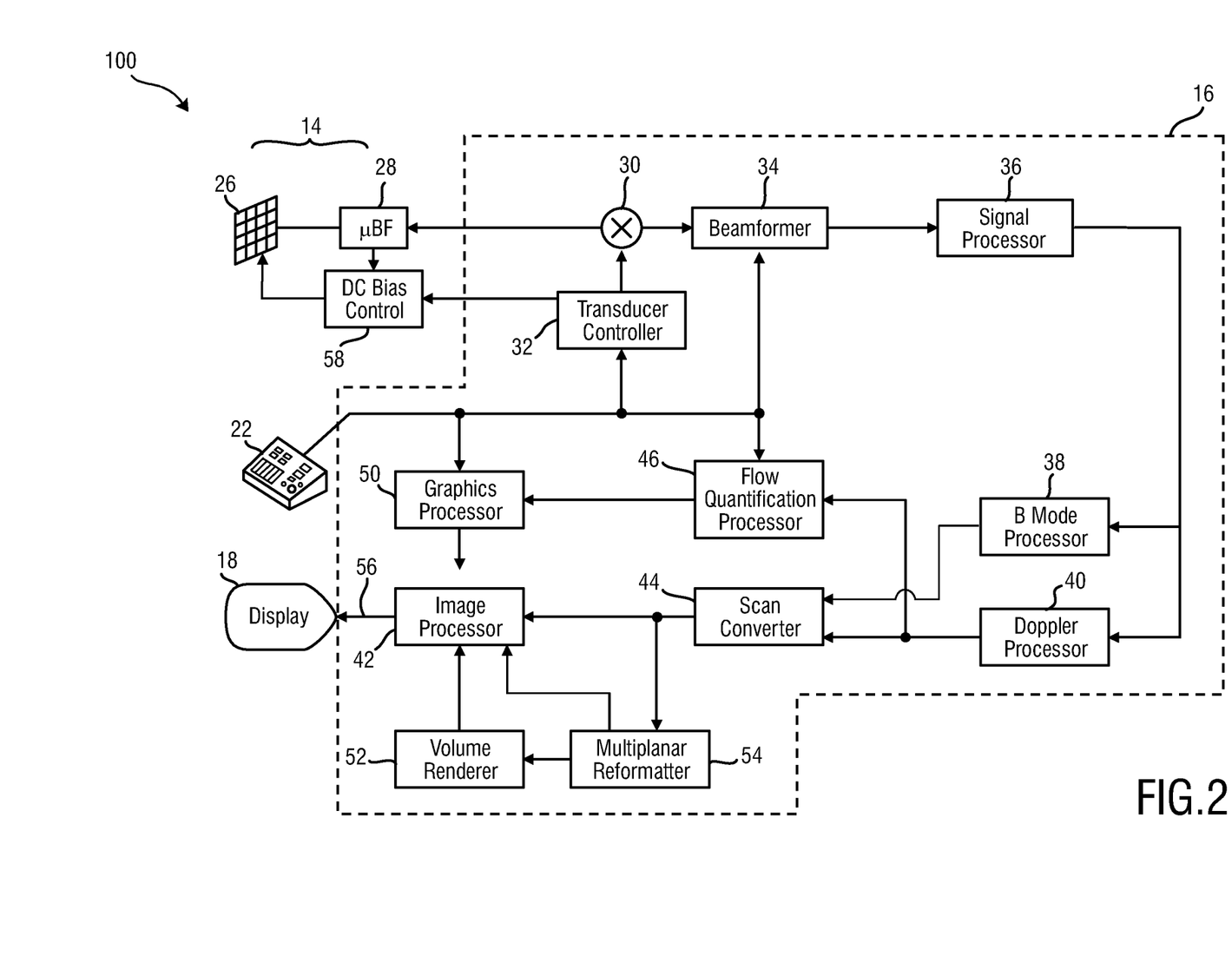
FIG. 2 shows a schematic block diagram of an embodiment of an ultrasound imaging system.

FIG. 2 illustrates a schematic block diagram of the ultrasound system 100. The ultrasound probe 14 may, for example, comprise a CMUT transducer array 26. The transducer array 26 may alternatively comprise piezoelectric transducer elements formed of materials such as PZT or PVDF. The transducer array 26 is a one- or a two-dimensional array of transducer elements capable of scanning in three dimensions for 3D imaging. The transducer array 26 is coupled to a microbeamformer 28 in the probe which controls transmission and reception of signals by the CMUT array cells or piezoelectric elements. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer 28 may coupled by a probe cable to a transmit/receive (T/R) switch 30 which switches between transmission and reception and protects the main beamformer 34 from high energy transmit signals when a microbeamformer 28 is not used and the transducer array 26 is operated directly by the main beamformer 34. The transmission of ultrasonic beams from the transducer array 26 under control of the microbeamformer 28 is directed by a transducer controller 32 coupled to the microbeamformer 28 by the T/R switch 30 and the main system beamformer 34, which receives input from the user's operation of the user interface or control panel 22. One of the functions controlled by the transducer controller 32 is the direction in which beams are steered and focused. Beams may be steered straight ahead from (orthogonal to) the transducer array 26, or at different angles for a wider field of view. The transducer controller 32 can be coupled to control a DC bias control 58 for the CMUT array. The DC bias control 58 sets DC bias voltage(s) that are applied to the CMUT cells.

The partially beamformed signals produced by the microbeamformer 26 on receive are coupled to the main beamformer 34 where partially beamformed signals from individual patches of transducer elements are combined into a fully beamformed signal. For example, the main beamformer 34 may have 128 channels, each of which receives a partially beamformed signal from a patch of dozens or hundreds of CMUT transducer cells or piezoelectric elements. In this way the signals received by thousands of transducer elements of the transducer array 26 can contribute efficiently to a single beamformed signal.

The beamformed signals are coupled to a signal processor 36. The signal processor 36 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and/or microbubbles comprised in a contrast agent that has been pre-administered to the body of the patient 12. The signal processor 36 may also perform additional signal enhancement such as speckle reduction, signal compounding, and noise elimination. The bandpass filter in the signal processor 36 can be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals may be transferred to a B mode processor 38 and a Doppler processor 40. The B mode processor 38 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.) The Doppler processor 40 may process temporally distinct signals from tissue movement and blood flow for the detection of the motion of substances such as the flow of blood cells in the image field. The Doppler processor 40 typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material. This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor 40 may receive and process a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B mode and Doppler processors 38, 40 may then be transferred to a scan converter 44 and a multiplanar reformatter 54. The scan converter 44 arranges the echo signals in the spatial relationship from which they were received in a desired image format. For instance, the scan converter 44 may arrange the echo signal into a two dimensional (2D) sector-shaped format, or a pyramidal three dimensional (3D) image. The scan converter 44 can overlay a B mode structural image with colors corresponding to motion at points in the image field with their Doppler-estimated velocities to produce a color Doppler image which depicts the motion of tissue and blood flow in the image field. The multiplanar reformatter 54 will convert echoes which are received from points in a common plane in a volumetric region of the body into an ultrasonic image of that plane, as described in U.S. Pat. No. 6,443,896 (Detmer). A volume renderer 52 converts the echo signals of a 3D data set into a projected 3D image sequence 56 over time as viewed from a given reference point as described in U.S. Pat. No. 6,530,885 (Entrekin et al.). The 3D image sequence 56 is transferred from the scan converter 44, multiplanar reformatter 54, and volume renderer 52 to an image processor 42 for further enhancement, buffering and temporary storage for display on the display 18. In addition to being used for imaging, the blood flow values produced by the Doppler processor 40 and tissue structure information produced by the B mode processor 38 may be transferred to a quantification processor 46. This quantification processor 46 may produce measures of different flow conditions such as the volume rate of blood flow as well as structural measurements such as the sizes of organs and gestational age. The quantification processor 46 may receive input from the user control panel 22, such as the point in the anatomy of an image where a measurement is to be made. Output data from the quantification processor 46 may be transferred to a graphics processor 50 for the reproduction of measurement graphics and values with the image on the display 18. The graphics processor 50 can also generate graphic overlays for display with the ultrasound images. These graphic overlays can contain standard identifying information such as patient name, date and time of the image, imaging parameters, and the like. For these purposes the graphics processor 50 may receive input from the user interface 22, such as patient name. The user interface 22 may be coupled to the transmit controller 32 to control the generation of ultrasound signals from the transducer array 26 and hence the images produced by the transducer array and the ultrasound system. The user interface 22 may also be coupled to the multiplanar reformatter 54 for selection and control of the planes of multiple multiplanar reformatted (MPR) images which may be used to perform quantified measures in the image field of the MPR images.

Again, it shall be noted that the aforementioned ultrasound system 100 has only been explained as one possible example for an application of the presented medical image processing device. It shall be noted that the aforementioned ultrasound system 100 does not have to comprise all of the components explained before. On the other hand, the ultrasound system 100 may also comprise further components, if necessary. Still further, it shall be noted that a plurality of the aforementioned components does not necessarily have to be realized as hardware, but may also be realized as software components. A plurality of the aforementioned components may also be comprised in common entities or even in one single entity and do not all have to be realized as separate entities, as this is schematically shown in FIG. 2.

Figure 3:
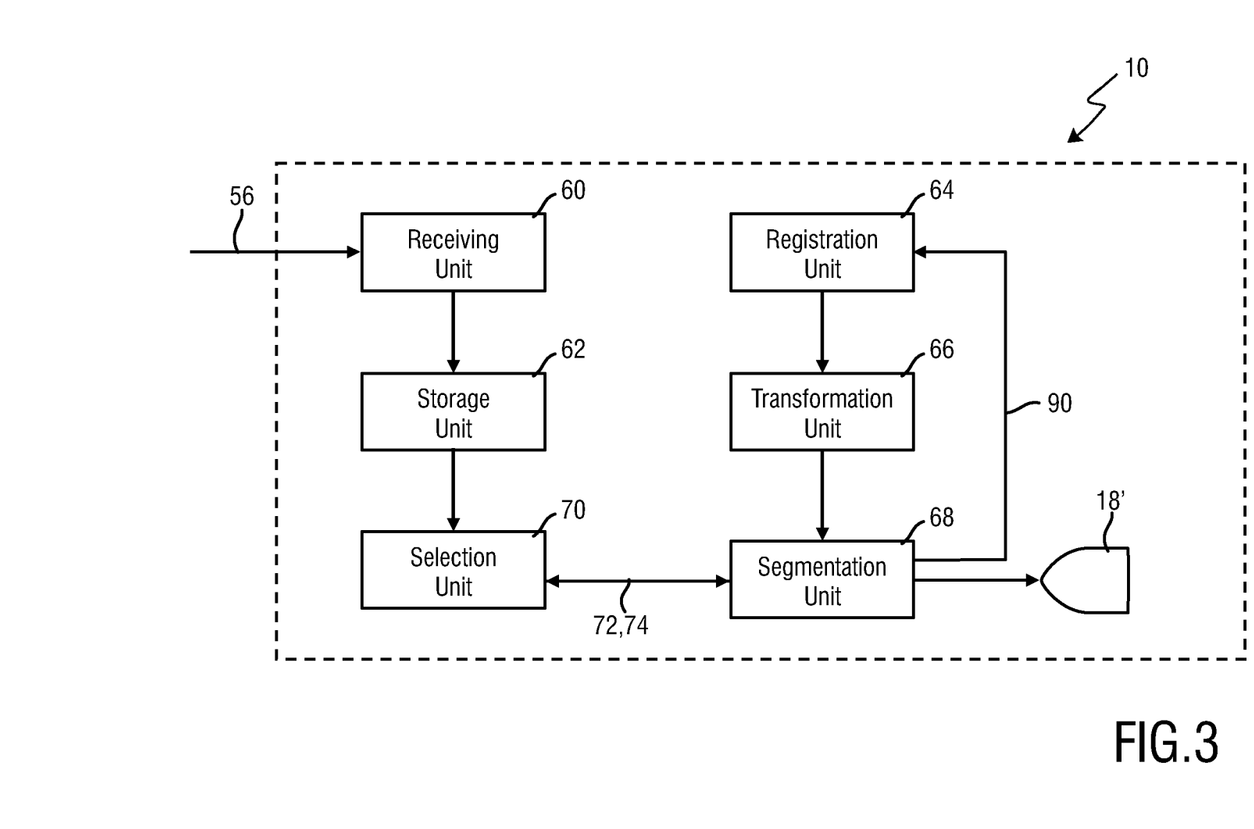
FIG. 3 shows a schematic block diagram of an embodiment of a medical image processing device according to the present invention.
Figure 4:
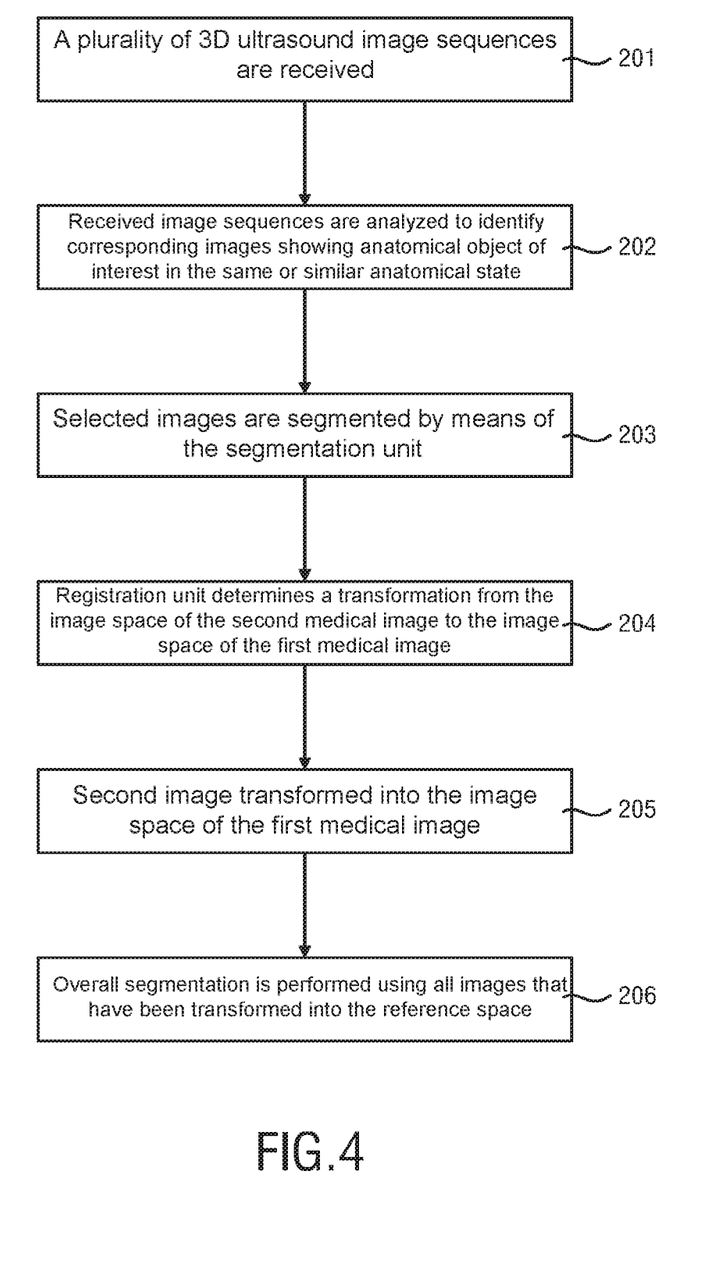
FIG. 4 shows a schematic block diagram of an embodiment of a corresponding medical image processing method according to the present invention.

FIG. 3 shows a schematic block diagram of an embodiment of the medical image processing device 10 according to the present invention. FIG. 4 shows a block diagram that schematically illustrates the corresponding medical image processing method according to the present invention. The technical principle of the presented device 10 and corresponding method will be in the following explained by means of an application for TTE images of the beating heart. However, it shall be noted that the presented device 10 and corresponding method may be similarly used for other applications in the field of medical imaging, such as e.g. for fetal ultrasound applications.

The main idea of the present invention is to present a device 10 and corresponding method that allow segmenting and quantifying the complete structure of an anatomical object of interest, for example of the heart, by using multiple medical images comprising different field of views and showing different sub-structures of the anatomical object of interest. This shall help to quantify the complete structure of the anatomical object of interest, even though each individual image shows only a particular part of the anatomical object of interest due to the limited field of view which is typical for ultrasound applications.

According to the embodiment shown in FIG. 3, the presented medical image processing device 10 comprises a receiving unit 60, a storage unit 62, a registration unit 64, a transformation unit 66, a segmentation unit 68 and a selection unit 70. All of the aforementioned units 60-70 may be implemented as hardware and/or software. All these units 60-70 may either be provided as individual, separate units, but may be also implemented in one and the same unit, e.g. in a processor or microprocessor.

The medical image processing device 10 may be realized as an entity that is separate from the above-mentioned ultrasound system 100. Alternatively, the medical image processing device 10 may be implemented as a part of the above-mentioned ultrasound system 100 and could be integrated into the image processor 42.

In a first step 201 of the herein presented method, a plurality of 3D ultrasound image sequences 56 are received by means of the receiving unit 60. These image sequences 56 may either be received in real-time from the ultrasound system 100 or, in an off-line mode, from any type of database into which pre-acquired image sequences 56 have been stored in advance. Each of the plurality of image sequences 56 comprises a plurality of frames (herein referred to as images). These timely-consecutive images form an image sequence showing the anatomical object of interest over time, e.g. showing the moving heart over one or more heart cycles. Each of these image sequences 56 comprises a different field of view of the anatomical object of interest, wherein e.g. one image sequence shows the left part of the heart including the left ventricle and another image sequence shows the right part of the heart including the right ventricle.

The received image sequences 56 may then be stored in the storage unit 62. This storage unit 62 may be a temporary storage.

In the next step 202, the received image sequences have to be analyzed in order to identify corresponding images showing the anatomical object of interest in the same or similar anatomical state. This means that from all different image sequences a specific image frame has to be selected, wherein each of the specific image frames show the anatomical object of interest in the same or similar anatomical state. In the given example of TTE images each image sequence 56 has to be scanned in order to find an image frame showing the heart in a specific cardiac phase, such as the end-diastolic phase or the end-systolic phase. The result of this selection step 202 is the identification of multiple images, wherein each image shows the heart in the same cardiac phase, and wherein each image is taken out of a different image sequence showing a different field of view of the heart.

This image selection may be done either manually by a user or derived automatically by means of the selection unit 70. In case of a manual selection the user has to manually select one image out of each received image sequence 56. Alternatively, the selection unit 70 may automatically select from each image sequence 56 an image showing the heart in a specific common cardiac phase. This may be done by individually segmenting all images of all image sequences 56 and deriving for each image sequence 56 a volume curve that is derived from the individual segmentations of the images of the corresponding image sequence 56. Said volume curve may, for example, show how the area surrounded by the segmentation mesh changes over the cardiac cycle of the heart. This helps to identify an image from each image sequence 56 that shows the heart in a specific cardiac phase.

Figure 5A:
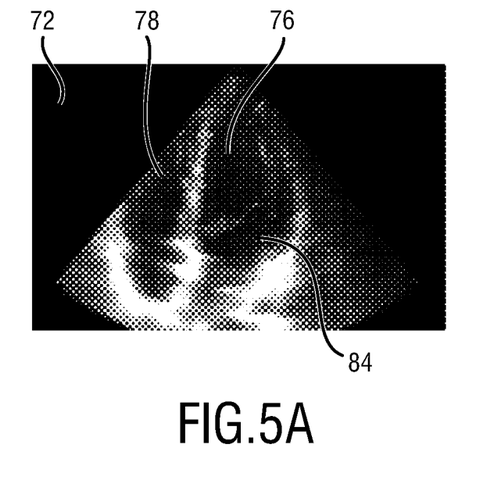
FIGS. 5A and 5B show examples of a first and a second medical image which may be processed by means of the medical image processing device according to the present invention.
Figure 5B:
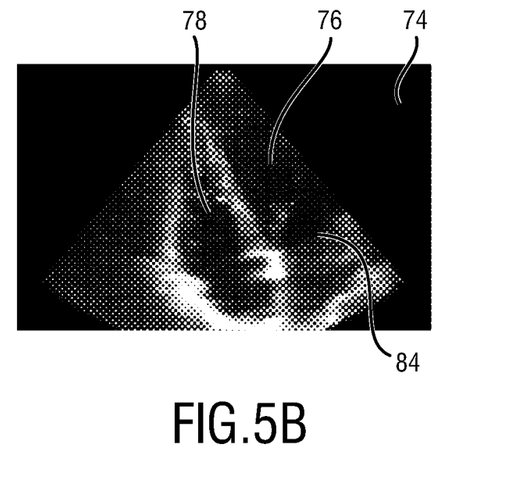
Figure 6A:
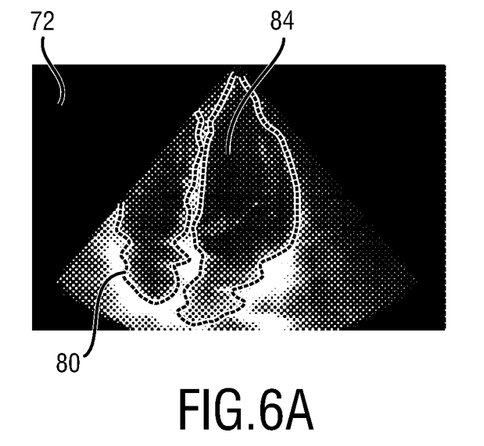
FIGS. 6A and 6B schematically illustrate an intermediary result of an individual segmentation of the first and the second medical image.
Figure 6B:
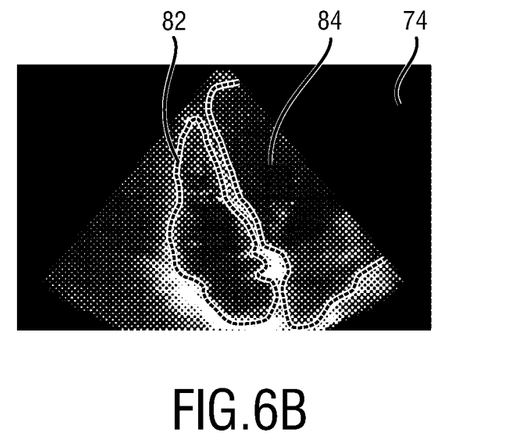

FIGS. 5A and 5B show two exemplary images, a first image 72 shown in FIG. 5A and a second image 74 shown in FIG. 5B, wherein both images show the heart in the same cardiac phase. By comparing FIGS. 5A and 5B with each other it may be observed that both images 72, 74 comprise a different field of view. The first image includes the whole left ventricle 76, but only a part of the right ventricle 78. Some parts of the right ventricle 78 are missing (not shown) in the first image 72. The second image 74 on the other hand shows the complete right ventricle 78, but only a part of the left ventricle 76, wherein other parts of the left ventricle 76 are outside of the field of view.

The selected images 72, 74 are in the next step 203 segmented by means of the segmentation unit 68, in case they have not been segmented yet in the selection step 202. The segmentation unit 68 thereto applies a model-based segmentation. In a first sub-step of this segmentation, the segmentation unit 68 identifies a first set of feature points 80 within the first image 72 that are approximately arranged on the contours of the heart 84. The same is done in the second image 74 in order to identify a second set of feature points 82. One possibility to identify these feature points 80, 82 is to identify image points having the highest brightness gradients within each of the first image 72 and the second image 74, respectively. It shall be noted that of course other characteristics, such as the absolute brightness values of each pixel and the neighboring pixels, may also be taken into account to identify the set of feature points 80, 82.

In the next sub-step of the segmentation 203, these feature points 80, 82 are used to adapt a segmentation mesh-model to each of the sets of feature points 80, 82. It shall be noted that both of these sub-steps of the segmentation 203 are usually done in one and the same step. The feature points 80, 82 are herein only visualized for illustration purposes. The result of the two individual segmentations of the first and the second image 72, 74 is shown in FIGS. 7A and 7B.

Figure 7A:
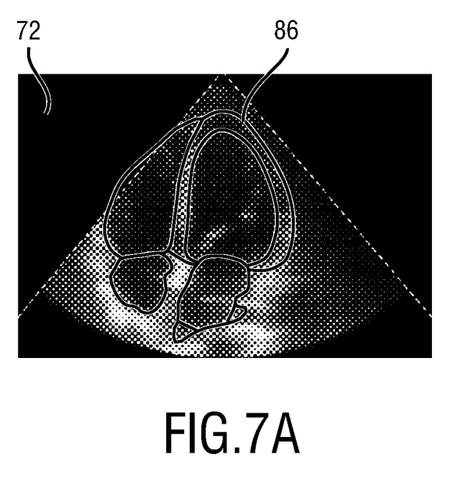
FIGS. 7A and 7B schematically illustrate a final result of the individual segmentation of the first and the second medical image.
Figure 7B:
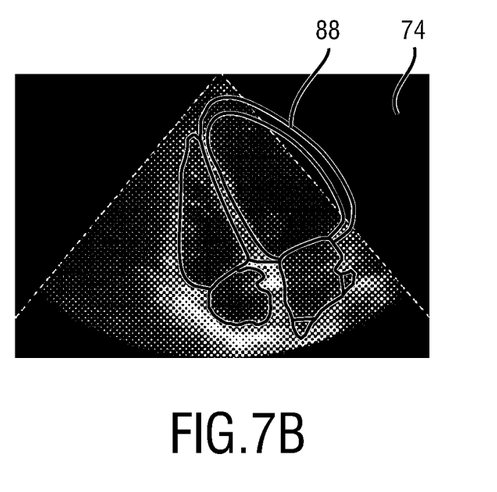

FIG. 7A shows a first segmentation mesh 86 that is overlaid over the first image 72. FIG. 7B shows a second segmentation mesh 88 that is overlaid over the second image 74. Both segmentation meshes 86, 88 may include different sub-meshes, wherein each sub-mesh is adapted to a specific sub-structure of the heart, e.g. one sub-mesh for the left ventricle and another sub-mesh for the right ventricle. The segmentation unit 68, however, preferably uses the same segmentation model 86, 88 for segmenting the first image 72 and the second image 74. Nevertheless, both images 72, 74 are in this step 203 segmented individually. It shall be furthermore noted that the segmentation meshes 86, 88 are three-dimensional surface meshes in case of three-dimensional images 72, 74.

The segmentation may be realized in a similar manner as this is described for a model-based segmentation of CT images in Ecabert, O. et al.: "Automatic model-based segmentation of the heart in CT images", IEEE transactions on medical imaging, vol. 27(9), pages 1189-1291, 2008, which is herein incorporated by reference. This model-based segmentation makes use of a geometrical mesh modal of the anatomical object of interest, and may comprise respective segments representing respective anatomic features of the anatomical object of interest. Such a model-based segmentation usually starts with the identification of the position and orientation of the anatomical object of interest within the image. This may, for example, be done using a Generalized Hough Transform. Pose misalignment may be corrected by matching the geometrical mesh model to the image, making use of a global similarity transformation. The segmentation comprises an initial model that roughly represents the shape of the anatomical features of the anatomical object of interest. Said model may be multi-compartment mesh model with triangular meshes. The initial model will be deformed by a transformation. This transformation is decomposed in two transformations of different kinds: a global transformation that can translate, rotate or rescale the initial shape of the geometrical model, if needed, and a local deformation that will actually deform the geometrical model so that it matches more precisely to the anatomical object of interest. This is usually done by defining the normal vectors of the surface of the geometrical model to match the image gradients; that is to say, the segmentation will look in the image for bright-to-dark edges (or dark-to-bright edges), which usually represent the tissue borders in the images, i.e. the boundaries of the anatomical object of interest.

It is clear that the above-mentioned individual segmentations are in practice not only applied to two images 72, 74, but to a plurality of images. The principle of the presented device 10 and the presented method shall herein for simplicity reasons however only be explained by means of two images 72, 74. In case of a plurality of images, the inventive principle stays the same.

Figure 8A:
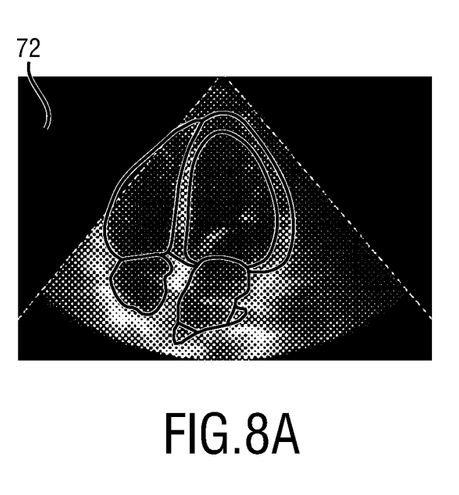
FIGS. 8A and 8B show the segmented first and (transformed) second medical image after an image registration and transformation.
Figure 8B:
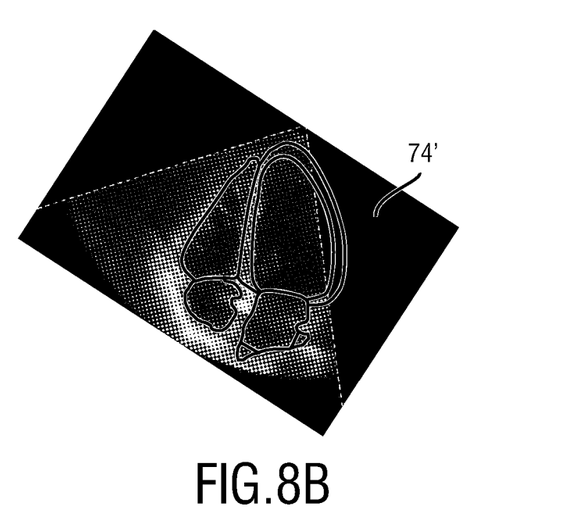

The segmented images 72, 74 will then be transferred to the registration unit 64 as indicated in FIG. 3 by arrow 90. In step 204, the registration unit 64 determines a transformation from the image space of the second medical image 74 to the image space of the first medical image 72. The registration unit 64 in other words determines the inter-field-of-view transformations from each selected image into a reference space/common coordinate system. In the shown example the image space of the first image 72 is used as reference space. The transformation from the image space of the second medical image 74 to the image space of the first medical image 72 is determined by applying a point-based registration of the second segmentation mesh 88 onto the first segmentation mesh 86. The individual segmentations applied in the prior step 203 may thus be used now for registering each image into the reference space by means of a point-wise, mesh-based registration that is used to estimate the inter-field-of-view transformation for each image. This transformation is a rigid transformation which models the translation and/or rotation of the ultrasound transducer probe. Using the determined inter-field-of-view transformation the second image 74 may then be transformed into the image space of the first medical image in step 205 by means of the transformation unit 66. Since the image space of the first image 72 is used as the reference image space, the first image 72 is in this exemplary case not transformed, while the transformation of the second image 74 results in a transformed second image 74'. The results of this transformation are exemplarily shown in FIGS. 8A and 8B. All selected images are thus now registered and transformed to the same reference space. The (transformed) images are then transferred to the segmentation unit 68 again.

Figure 9:
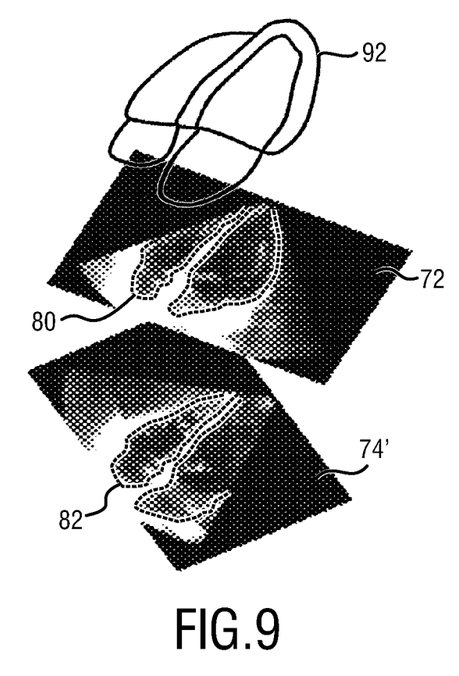
FIG. 9 schematically illustrates an overall segmentation using both the first medical image and the transformed second medical image.

The segmentation unit 68 finally performs in step 206 an overall segmentation that uses all images that have been transformed into the reference space. In the exemplarily shown example the segmentation unit 68 performs an overall segmentation that makes use of the first medical image 72 and the transformed second medical image 74'. However, it is important to note that the images 72, 74' are in this case not segmented individually (as in step 203), but segmented together in a single overall segmentation. The segmentation unit 68 thereto adapts one and the same segmentation mesh-model simultaneously to both the first medical image 72 and the transformed second medical image 74'. This step is schematically illustrated in FIG. 9.

The overall segmentation mesh-model 92 will thus be adapted to both the first set of feature points 80 within the first medical image 72 as well as to the second set of feature points 82 within the transformed second medical image 74'. The overall segmentation mesh-model 92 used in this step may be a similar mesh-model as used for the individual segmentations in step 203. The difference is, however, that the overall segmentation mesh-model 92 is in the overlapping regions of the first and the transformed second image 72, 74' adapted to both feature points 80, 82 in said region, whereas it is adapted in the non-overlapping image regions either adapted to the feature points 80 of the first medical image 72 or to the feature points 82 of the transformed second medical image 74'. Consequently, a single segmentation of the whole anatomical object of interest (here the heart 84) is computed from a collection of several different images showing different field of views, such that each sub-structure of the heart 84 is segmented from those images where it is visible in. In the end a single consistent overall segmentation of the whole heart 84 is obtained allowing an overall quantification of the heart 84.

As already mentioned in the introductory portion of the description, it is important to note that said overall segmentation model 92 is in contrast to the approach proposed by Rajpoot, K. et al. not adapted to a fused imaged. During the overall segmentation in step 206, the different medical images 72, 74' are still separately stored in the storage unit 62 without fusing them. Only the overall mesh-model 92 is deformed to match the detected image points 80, 82 from all images 72, 74'. This leads to a very robust and accurate segmentation of the whole heart 84.

Figure 10:
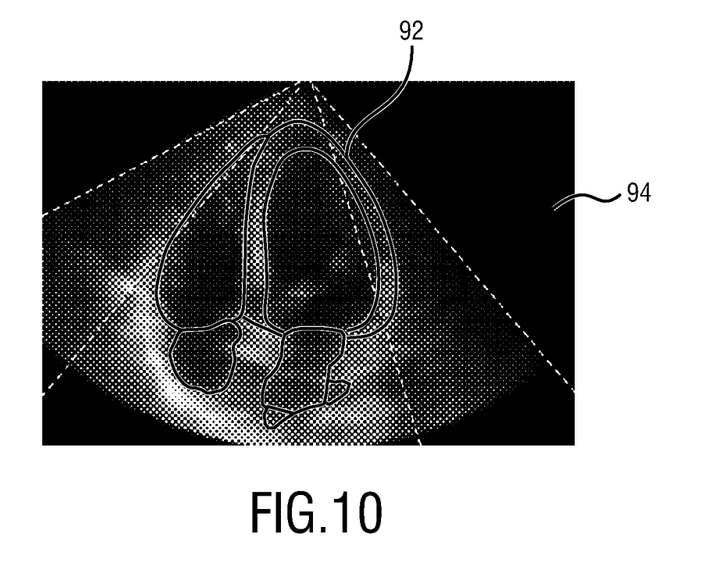
FIG. 10 shows a fused image of the first medical image and the transformed second medical image.

The first and the second transformed medical image 72, 74' may nevertheless be fused in an optional step, if this is needed. Such a fused exemplary image 94 is shown in FIG. 10. This fused image 94 may be provided as an add-on for visualization purposes. However, the fused image 94 has actually no connection to the overall segmentation mesh-model 92 that results from step 206.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A medical image processing device, comprising: one or more processors configured to:
   receive a first and a second medical image of an anatomical object of interest, wherein each of the first and the second medical images comprises a different field of view of the anatomical object of interest, and wherein the first medical image and the second medical image show a same or similar anatomical state of the anatomical object of interest;
   perform an individual segmentation of the first medical image in order to receive a first segmentation mesh;
   perform a second individual segmentation of the second medical image in order to receive a second segmentation mesh;
   determine a transformation from an image space of the second medical image to an image space of the first medical image, wherein the transformation is determined by applying a point-based registration of the second segmentation mesh onto the first segmentation mesh;
   transform the second medical image into the image space of the first medical image based on said transformation in order to receive a transformed second medical image; and
   perform an overall segmentation that makes a separate use of both the first medical image and the transformed second medical image by identifying a first set of feature points of the anatomical object of interest within the first medical image and by identifying a second set of feature points of the anatomical object of interest within the transformed second medical image;
   wherein one and the same segmentation model is simultaneously adapted to both the first medical image and the transformed second medical image by adapting the segmentation model to both the first and the second set of feature points.

2. The medical image processing device according to claim 1, wherein the one or more processors are configured to identify the first and the second set of feature points of the anatomical object of interest by identifying within each of the first medical image and the transformed second medical image points having the highest brightness gradients within each of the first medical image and the transformed second medical image, respectively.

3. The medical image processing device according to claim 1, wherein the one or more processors are configured to apply the same segmentation model for the individual segmentation of the first medical image and the second medical image.

4. The medical image processing device according to claim 1, wherein the one or more processors are configured to receive a first medical image sequence including the first medical image and a second medical image sequence including the second medical image, and wherein the one or more processors are further configured for selecting the first and the second medical image in order to identify corresponding images of the same or similar anatomical state of the anatomical object of interest.

5. The medical image processing device according to claim 4, wherein the one or more processors are configured to individually segment all images of the first and the second medical image sequence, and wherein the one or more processors are configured to automatically select the first and the second medical image based on the segmentation of all images of the first and the second medical image sequence.

6. The medical image processing device according to claim 1, wherein the one or more processors are configured to reconstruct a fused image by fusing the first medical image and the transformed second medical image.

7. The medical image processing device according to claim 1, wherein the first medical image and the second medical image are three-dimensional transthoracic echocardiographic images, 3D transesophageal echocardiographic images or three-dimensional fetal ultrasound images.

8. An ultrasound system, comprising:
an ultrasound transducer for transmitting and receiving ultrasound waves to and from the anatomical object of interest;
one or more processors configured for reconstructing the first medical image and the second medical image from the ultrasound waves received from the anatomical object of interest; and
the medical image processing device claimed in claim 1.

9. A medical image processing method, wherein the method comprises the steps of:
receiving a first medical image and a second medical image of an anatomical object of interest, wherein each of the first and the second medical images comprises a different field of view of the anatomical object of interest, and wherein the first medical image and the second medical image show a same or similar anatomical state of the anatomical object of interest;
performing an individual segmentation of the first medical image in order to receive a first segmentation mesh;
performing an individual segmentation of the second medical image in order to receive a second segmentation mesh;
applying a point-based registration of the second segmentation mesh onto the first segmentation mesh to determine a transformation from an image space of the second medical image to an image space of the first medical image;
transforming the second medical image into the image space of the first medical image based on said transformation in order to receive a transformed second medical image; and
performing an overall segmentation that makes a separate use of both the first medical image and the transformed second medical image by identifying a first set of feature points of the anatomical object of interest within the first medical image and by identifying a second set of feature points of the anatomical object of interest within the transformed second medical image, wherein one and the same segmentation model is simultaneously adapted to both the first medical image and the transformed second medical image by adapting the segmentation model to both the first and the second set of feature points.

10. A computer program product comprising a tangible computer-readable medium comprising executable instructions for causing a computer to carry out the steps of the method as claimed in claim 9.

11. The medical image processing device of claim 1, wherein the first segmentation mesh comprises a first sub-mesh corresponding to a first sub-structure of the anatomical object of interest, and the second segmentation mesh comprises a second sub-mesh corresponding to a different second sub-structure of the anatomical object of interest.

12. The medical image processing device according to claim 1, wherein the one or more processors are configured to:
perform the individual segmentation of the first medical image using a first segmentation mesh-model;
perform the second individual segmentation of the second medical image using a second segmentation mesh-model; and
perform the overall segmentation using a third segmentation mesh-model.

13. The medical image processing device of claim 12, wherein the first segmentation mesh-model is adapted to the first medical image to produce the first segmentation mesh, and the second segmentation mesh-model is adapted to the second medical image to produce the second segmentation mesh.

14. The medical image processing device of claim 12, wherein:
performing the individual segmentation of the first medical image comprises adapting the first segmentation mesh-model to each of the first set of feature points to generate the first segmentation mesh; and
performing the individual segmentation of the second medical image comprises adapting the second segmentation mesh-model to each of the second set of feature points to generate the second segmentation mesh.

15. The medical image processing device of claim 12, wherein:
performing the overall segmentation comprises:
in a first region of the anatomical object of interest included in both the first medical image and the transformed second medical image, adapting the third segmentation mesh-model to a first subset of feature points of the first set of feature points and a first subset of feature points of the second set of feature points;
in a second region of the anatomical object of interest included in only the first medical image, adapting the third segmentation mesh-model to a second sub-set of feature points of the first set of features points; and
in a third region of the anatomical object of interest included in only the transformed second medical image, adapting the third segmentation mesh-model to a second sub-set of feature points of the second set of features points.

\* \* \* \* \*